(12) United States Patent
Ferguson et al.

(10) Patent No.: US 9,486,204 B1
(45) Date of Patent: Nov. 8, 2016

(54) SUTURE ASSEMBLY FOR CRANIAL CRUCIATE LIGAMENT SURGERY

(71) Applicant: RIVER POINT, LLC, Portland, OR (US)

(72) Inventors: Patrick Edward Ferguson, Portland, OR (US); Patrick Joseph Ferguson, Portland, OR (US)

(73) Assignee: RIVERPOINT MEDICAL, LLC, Portland, OR (US)

( * ) Notice: Subject to any disclaimer, the term of this patent is extended or adjusted under 35 U.S.C. 154(b) by 275 days.

(21) Appl. No.: 14/285,755

(22) Filed: May 23, 2014

(51) Int. Cl.
*A61B 17/04* (2006.01)

(52) U.S. Cl.
CPC ...... *A61B 17/0401* (2013.01); *A61B 2017/044* (2013.01); *A61B 2017/0464* (2013.01)

(58) Field of Classification Search
CPC ............... A61B 17/0401; A61B 2017/06185; A61B 17/06166; A61B 2017/044; A61B 2017/0414; A61B 17/0469; A61B 17/0485; A61B 17/1675; A61B 17/8061; A61B 17/864; A61F 2002/0882; A61F 2/0811; A61F 2002/0888; A61F 2/08; A61F 2002/087; A61F 2/0805
USPC ......... 606/232, 304; 623/13.14, 13.11, 13.13
See application file for complete search history.

(56) References Cited

U.S. PATENT DOCUMENTS

| | | | |
|---|---|---|---|
| 6,296,659 B1 | 10/2001 | Foerster | |
| 6,533,802 B2 | 3/2003 | Bojarski et al. | |
| 7,959,650 B2 | 6/2011 | Kaiser et al. | |
| 8,088,130 B2 | 1/2012 | Kaiser et al. | |
| 8,231,654 B2 | 7/2012 | Kaiser et al. | |
| 8,298,284 B2 | 10/2012 | Cassani | |
| 2008/0177302 A1 | 7/2008 | Shurnas | |
| 2010/0268273 A1 | 10/2010 | Albertorio et al. | |
| 2011/0087280 A1 | 4/2011 | Albertorio | |
| 2011/0098727 A1 | 4/2011 | Kaiser et al. | |
| 2011/0319945 A1* | 12/2011 | Tepic | A61B 17/0401 606/305 |
| 2012/0046746 A1 | 2/2012 | Konicek | |
| 2012/0123541 A1 | 5/2012 | Albertorio et al. | |
| 2013/0110165 A1 | 5/2013 | Burkhart et al. | |
| 2013/0317544 A1 | 11/2013 | Ferguson et al. | |

FOREIGN PATENT DOCUMENTS

WO WO 2014/076470 * 5/2014

* cited by examiner

*Primary Examiner* — Katherine M Shi
(74) *Attorney, Agent, or Firm* — Timothy E. Siegel Patent Law, PLLC; Timothy E. Siegel

(57) ABSTRACT

A method of repairing a stifle, including a first stifle bone and a second stifle bone in engaged opposition to the first stifle bone. The method begins with screwing a first bone screw into the first stifle bone and screwing a second bone screw, having an aperture in its shank, into the second stifle bone. Next, a tension member is used to pull a suture loop, to engage a portion of the suture loop about the shank of the first bone screw. Then, the tension member is used to pull the suture loop through the aperture of the second bone screw and then into engagement about the shank of the second bone screw.

5 Claims, 9 Drawing Sheets

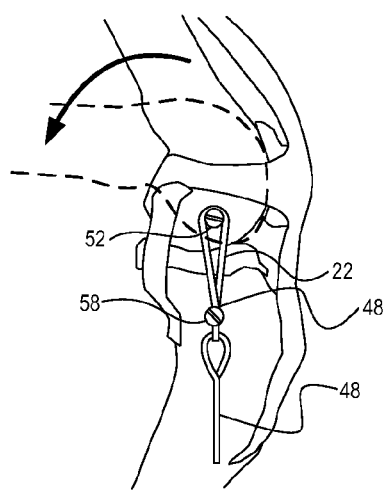
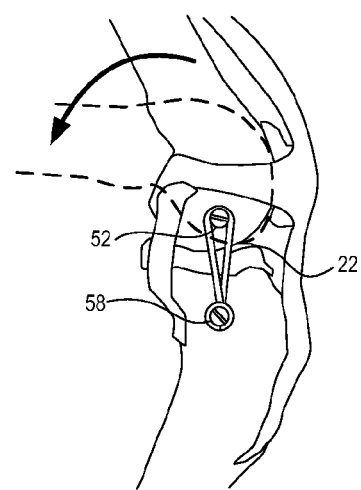
Fig. 18c  Fig. 18d

SUTURE ASSEMBLY FOR CRANIAL CRUCIATE LIGAMENT SURGERY

BACKGROUND

Currently, in the United States, many more cruciate ligament repair surgeries are performed on dogs than on people. Unfortunately, there is broad recognition that the available surgical procedures are sadly wanting in the degree to which the stifle (front knee joint of a dog) is repaired, and the durability of the repair. An improved technique and assembly for performing the technique is needed.

SUMMARY

The following embodiments and aspects thereof are described and illustrated in conjunction with systems, tools and methods which are meant to be exemplary and illustrative, not limiting in scope. In various embodiments, one or more of the above-described problems have been reduced or eliminated, while other embodiments are directed to other improvements.

In a first separate aspect, the present invention may take the form of a repaired front stifle having a first stifle bone and a second stifle bone in opposed engagement to the first stifle bone, and having a first bone screw, having a head, and a shank fastened into the first stifle bone. A second bone screw having a head and a shank and having a through-hole in the shank, adjacent to the head, is fastened into the second stifle bone. Finally, a suture loop, is slidingly retained between the shaft of the first bone screw and the first stifle bone, and extends through the through-hole of the second bone screw and around the shank of the second bone screw.

In a second separate aspect, the present invention may take the form of a suture assembly that includes a suture loop, having a suture length comprised of woven material that is circular in cross-section, thereby defining a lumen. A tail of the suture length extends through the woven material to enter the lumen and is engaged within the lumen, thereby forming a loop. Further, a tension member is engaged to the suture loop.

In a third separate aspect, the present invention may take the form of a method of repairing a stifle, including a first stifle bone and a second stifle bone in engaged opposition to the first stifle bone. The method begins with screwing a first bone screw into the first stifle bone and screwing a second bone screw, having an aperture in its shank, into the second stifle bone. Next, a tension member is used to pull a suture loop, to engage a portion of the suture loop about the shank of the first bone screw. Then, the tension member is used to pull the suture loop through the aperture of the second bone screw and then into engagement about the shank of the second bone screw.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced drawings. It is intended that the embodiments and figures disclosed herein are to be considered illustrative rather than restrictive.

FIGS. 18A-18D are successive steps in a cranial cruciate ligament repair surgery that utilizes the suture assembly of FIG. 15, and the screws of FIG. 17.

DETAILED DESCRIPTION OF THE PREFERRED EMBODIMENTS

Definitions

Bone screw: a screw having a head and an attached shank, and wherein the shank comes to a point at its end, to enable its introduction into bone.

Embodiments of the present invention are described below with reference to the above described figures. It is, however, expressly noted that the present invention is not limited to the embodiments depicted in the figures, but rather the intention is that modifications that are apparent to the person skilled in the art and equivalents thereof are also included.

Figure 1:
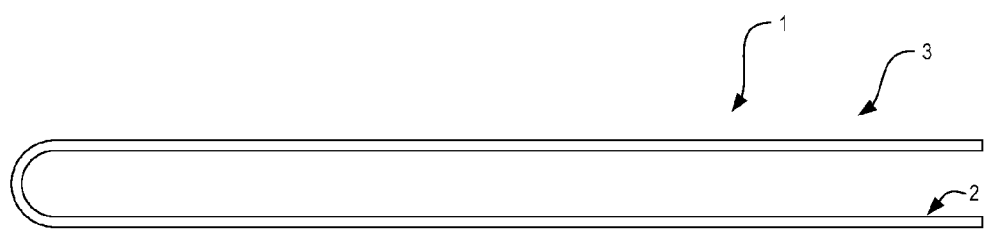
FIG. 1 is a side view of a length of suture material, formed into a U, and to be used in a further part of the production of a suture assembly according to the present invention.

FIG. 1 shows an open fiber 1 having two tails: a save tail 3 and a cut tail 2. According to preferred embodiments, the fiber 1 is a biocompatible fiber, such as an ultra-high molecular weight polyethylene (UHMWPE) fiber, although suitable non-preferred materials can be used as well including polyester and POLYBLEND®, for example. Additionally, the fiber 1 is braided as opposed to being monofilamentous. Braided fibers are particularly advantageous in the teachings herein as they are stronger and define a lumen therein, which allows for the tails 3 and 2 to be threaded into the lumen as will be discussed in more detail below.

Figure 2:
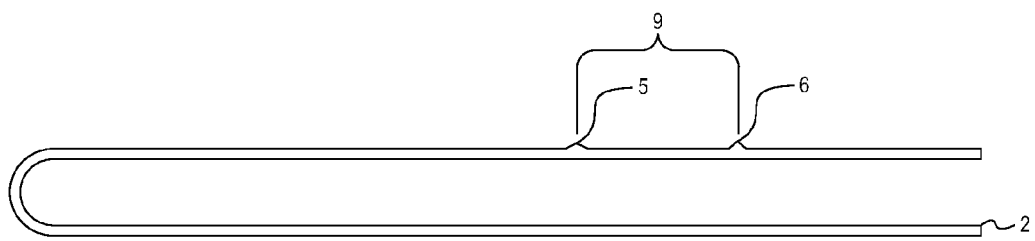
FIG. 2 is a side view of the material of FIG. 10, in a further step in the process of forming the length of suture material of FIG. 10 into a portion of the suture assembly of the present invention.

Referring to FIG. 2, an entry point 5 and an exit point 6 points can be designated along length of fiber 1 to define a middle section 9. Save tail 3 includes all of fiber 1, from exit point 6, to the nearest end point, as shown. Table I can be utilized as an approximate guide to determine suitable lengths of the starting fiber 1, save tail 3, and middle section 9 based on the final loop size desired. For example if a 20 mm final loop size is desired, it would be advantageous to begin with a thread having a length of about 6 inches (152.4 mm), and to configure the thread such that the middle section is 35 mm in length and the save tail section is 40 mm in length. Loop size is measured from the largest inner diameter of the loop formed from fiber 1, as described below.

TABLE I

| Loop Size (mm) | Fiber Length (in) | Save Tail Length (mm) | Middle Section Length (mm) | Pre-Stretch Length (mm) |
|---|---|---|---|---|
| 15 | 6 | 40 | 30 | ~13 |
| 20 | 6 | 40 | 35 | ~18 |
| 25 | 7 | 40 | 45 | ~23 |
| 30 | 8 | 45 | 60 | ~28 |
| 35 | 8 | 50 | 65 | ~33 |
| 40 | 10 | 55 | 75 | ~38 |

As shown in FIG. 2, the fiber 1 is preferably fluffed at the entry 5 and exit 6 points to make it easier for a lacing tool 7 (FIGS. 3-5) to be inserted through the middle section 9. One end of the lacing tool 7 (FIGS. 3-5) can include a handle to allow a user to position, guide, push, and pull the tool. The lacing tool 7 (FIGS. 3-5) also includes a main body that is preferably substantially linear and having a diameter, or cross-section, small enough to thread through the fiber 1. The end of the lacing tool 7 (FIGS. 3-5) opposite of the handle can include a hinged barb 10 to allow for coupling to the fiber 1. The hinge allows the barb 10 to have a lower profile when traversing through the inside of fiber 1 while minimizing the chance of snags. Other means for coupling to the fiber are readily contemplated and can non-exclusively include one or more barbs (hinged or unhinged) hooks, clamps (such that can be opened and closed by the handle) and the like, for example. Said means for coupling 10 preferably should not prevent or hinder the lacing tool 7 (FIGS. 3-5) from being pushed into or pulled out of the inside of the fiber 1.

Figure 3:
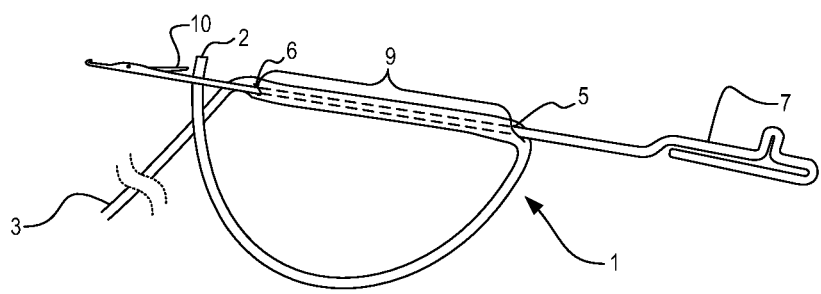
FIG. 3 is an isometric view of a length of suture material and a lacing tool that is being used to form the suture material into a suture loop, which forms a portion of a suture assembly according to the present invention.
Figure 4:
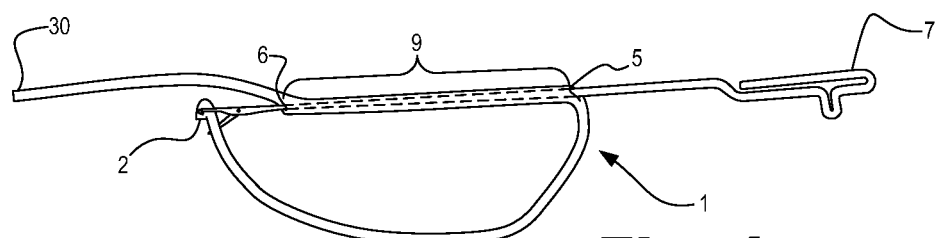
FIGS. 4-9 are isometric views of the elements of FIG. 3, in a series of further steps in the process of forming the suture assembly.
Figure 5:
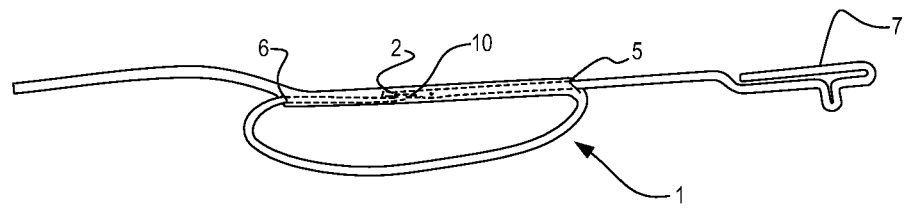
Figure 6:
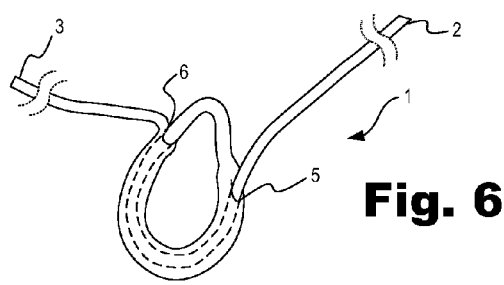
Figure 7:
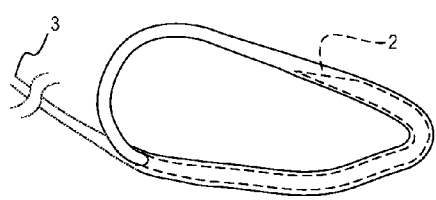

As depicted in FIGS. 3-5, once the middle section 9 is defined, the barb 10 of the lacing tool 7 is pushed into the lumen of the fiber 1 at the fluffed entry point 5. The barb 10 is pushed through the inside of the middle section 9 and guided outward through the fluffed exit point 6. With reference to FIGS. 4 and 5, the cut tail 2 is then coupled to the barb 10 and configured to allow the lacing tool 7 and cut tail 2 to be pulled back into the middle section 9 at the exit point 6. The barb 10 and coupled cut tail 2 are pulled out of the middle section 9 at the entry point 5. As shown in FIG. 6, this step results in general loop shape with the cut tail section 2 being exposed out of the fiber 1 at the entry point 5. The exposed cut tail 2 can be cut as close to the entry point 5 as possible, utilizing one or more of the following: scissors, knife, cutting instrument, thermal knife, and/or razor blade, and the like while avoiding cutting the external fiber near the entry point 5. The remaining cut tail 2 can be retracted within the lumen of the fiber through the entry point 5, as shown in FIG. 7 by any suitable method, such as by manually or mechanically stretching the loop. One preferred method is to utilize needle holders to cinch the loop. For example, the closed jaws of needle holders or a scissor-like tool can be inserted into the loop then opened to stretch the loop. A preferred machine could be a force gauge.

Next, second entry 15 and exit 16 points (FIG. 8) are defined along the fiber 1. The second exit point 16 can preferably be positioned within close proximity to the end of the retracted cut tail 2 to minimize the amount of external fiber outside the loop lumen while still allowing for an internal overlap, or proximity, between the save tail and cut tail 2 and 3 within the lumen. These second entry 15 and exit 16 points can also be fluffed to allow for the lacing tool 7 to readily enter and exit the fiber 1. After the second entry 15 and exit 16 points are defined, the barb 10 of the lacing tool 7 is pushed into the lumen of the fiber 1 at the fluffed second entry point 15. The barb 10 is pushed through the inside of the fiber 1 and guided outward through the fluffed second exit point 16. In one preferred embodiment, the assembly is essentially finished at this point, with the save tail being cut close to entry point 5, to avoid having an unnecessary loose end. The reinforcing regions 20 and 21, noted below and in FIG. 10, may then be applied, but simply to entry point 5 or to the location of cut end 2.

Figure 9:
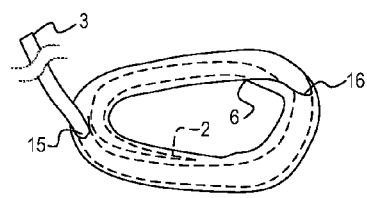

The save tail 3 is then coupled to the barb 10 and configured to allow the lacing tool 7 and save tail 3 to be pulled back into fiber 1 at the second exit point 16. The barb 10 and coupled save tail 3 can be pulled out of fiber's lumen at the second entry point 15. As shown in FIG. 9, this step results with the save tail section 3 being exposed out of the fiber 1. The exposed save tail 3 is preferably cut near the second entry point 15, such that a small section of the save tail 3 is still exposed. Cutting can be done utilizing one or more of the following: scissors, knife, cutting instrument, thermal knife, and/or razor blade, and the like while avoiding cutting the external fiber near the second entry point 15.

After the save tail 3 is initially cut, it is preferred to manually or mechanically expand the loop, thereby causing fiber 1 to contract in transverse dimension, so that it is in closer engagement with tails 2 and 3. One preferred method is to utilize needle holders to cinch the loop. For example, the closed jaws of needle holders or a scissor-like tool can be inserted into the loop then opened to stretch the loop. A preferred machine could be a force gauge. The inner diameter of the loop can be measured to determine how close it is to the final desired size. If needed, the loop can be stretched using tools or machines prior to the stitching/securing steps described below. As a preferred example, the fiber loop can be manually or mechanically stretched to approximately 100 lbs. One type of suitable machine that can be used for this step is a force gauge.

Figure 8:
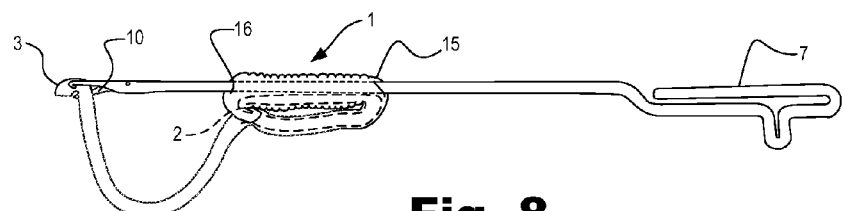
Figure 11:
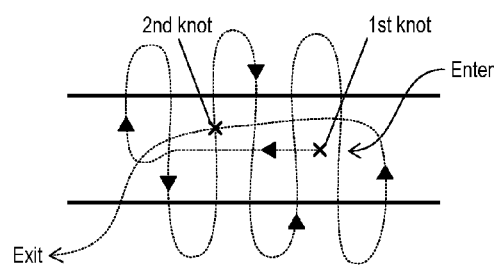
FIG. 11 is an illustration of a stitching pattern used in part of suture assembly used in one embodiment of the present invention.
Figure 10:
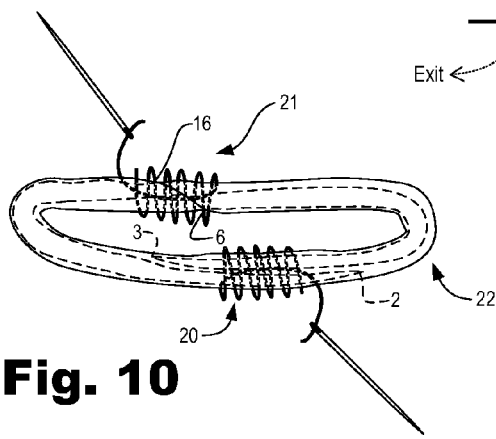
FIG. 10 is an isometric view of a final step in the production of one variant of a suture loop, which forms a part of a suture assembly according to the present invention.
Figure 12:
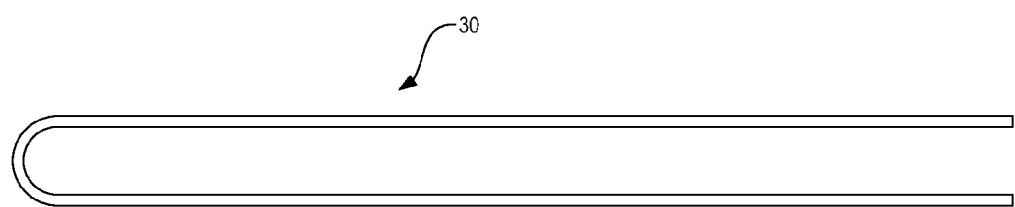
FIG. 12 is a side view of a length of suture material, formed into a U, and to be used in a further part of the production of a suture assembly according to the present invention.
Figure 13:
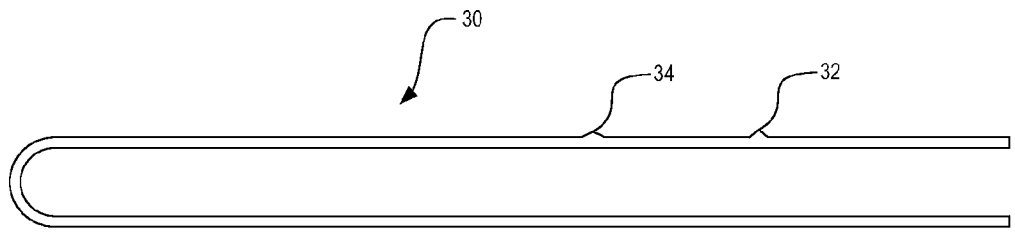
FIG. 13 is a side view of the material of FIG. 12, in a further step in the process of forming the length of suture material of FIG. 12 into a portion of the suture assembly of the present invention.
Figure 14:
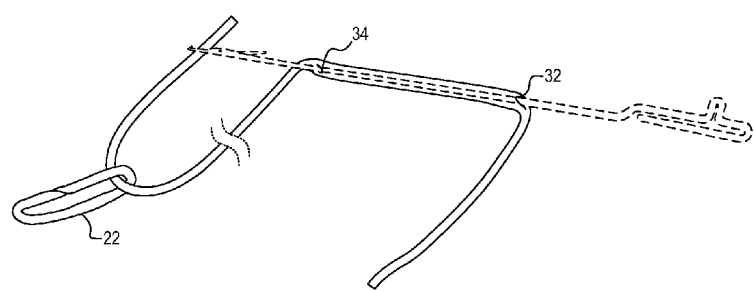
FIG. 14 is an isometric view showing a lancing tool arranging the suture of FIG. 12, so that it interlocks with the suture loop of FIG. 11.

In one preferred embodiment the stitching steps shown in FIGS. 10 and 11 are not performed, with the natural engagement of the interior surface of fiber 1 with tails 2 and 3, holding tails 2 and 3 in place. As shown in FIG. 10, a first stitching section 21 is defined by a section on the fiber 1 that encompasses the first exit point 6 where the cut tail 2 has entered into the lumen. As shown in FIG. 10, a second stitching section 20 is defined by a section on the fiber 1 that encompasses the ends of the cut tail 2 and the save tail 3. It is important to note that the location of the first and second entry and exit points 5, 6, 15, and 16 on the fiber 1 in FIGS. 8-10 are non-limiting, as they can be positioned closer to each other or at different locations depending on the final size of the assembly. A needle 25 and thread 23, such as UHMWPE thread, can be used to readily secure the first exit point 6 at the first stitching section 21 and the cut tail 2 and save tail 3 together at stitching section 20. Additionally, other means for securing or reinforcing sections 20, 21, besides stitching, can also readily be used. Non-exclusive examples, of securing or reinforcing means can include one or more adhesives, such as glue, heat setting, crimping. These means can be used by themselves or in conjunction with each other, or in conjunction with stitching.

After the first section 21, having the first exit point 6 is stitched, or otherwise secured or reinforced, it is preferred to stitch or otherwise secure the second stitching section 20 where the cut tail 2 and save tail 3 overlap, or are otherwise in close proximity. According to one method, stitching using a needle 25 and thread 23, such as an UHMWPE thread, can begin below the second entry point 15, such that the stitching moves in an upwards direction towards the second entry point 15. Alternatively, and as shown in FIG. 10, the stitching or reinforcing method can be started above the final section 20. FIG. 11 illustrates a preferred directional path of stitching along the fiber 1.

If the stitching reaches a position adjacent and below or above the second entry point 15, it is preferred to cut off the remaining exposed save tail 3 as close to the second entry point 15 as possible using any suitable cutting instrument, such as a razor blade, while not cutting, and thereby comprising the fiber 1. Alternatively, this could be the first cut of the exposed save tail 3 as opposed to the second cut. The remaining save tail 3 can be retracted within the lumen of the fiber 1 through the second entry point 15 as shown in FIG. 10. The save tail 3 can be retracted into the fiber using any suitable method, such as by utilizing needle holders, as described above, or by other manual or mechanical methods of stretching the fiber loop. It is preferred that the save tail 3 is retracted within the lumen in close approximation, or on the same side of the loop, as the retracted cut tail 2. More specifically, and as shown in FIG. 10, the save tail 3 and cut tail 2 are preferably aligned adjacent to each other to create an overlap of about ⅙-¼ of an inch depending on the final loop size desired (e.g., 15-60 mm). Additionally, the ends of the cut tail 2 and save tail 3 can be adjacent to each other, or alternatively there could be a small gap between the cut tail 2 and save tail 3.

Once the save tail 3 is fully retracted within the lumen, and positioned overlapping or near the cut tail 2, it is preferred to finalize the stitching in the second section 20. Stitching, or otherwise securing, the cut tail 2 and save tail 3 together helps prevent fraying of the fiber 1. As with the first section 21, the second section 20 can be secured or reinforced utilizing other means besides thread and needles stitching. Non-exclusive examples, of securing means can include one or more adhesives, such as glue, heat setting or crimping. These means can be used by themselves or in conjunction with each other, or in conjunction with stitching. According to other embodiments, the save tail 3 can first be retracted within the lumen, and then stitching or securing of the second section 20 can begin. Stitching or securing of the second section 20 advantageously secures the cut tail 2 and save tail 3 together within the braid 1 and to the braided fiber 1.

According to certain embodiments, the loop 22 can have only one stitched or reinforced section 20 or 21, and no more. This single reinforced section can be the section shown in 21 that covers the first exit point 6, where the cut tail 2 enters into the lumen of the fiber 1. Under this embodiment, the ends of the cut tail 2 and save tail 3 would not be connected within the lumen of the fiber 1. Alternatively, the single stitched or reinforced section can be the second section 20 that encompasses the cut tail 2 and save tail 3 junction within the lumen, without reinforcing the first exit point 6. Additional embodiments include having one or more of the reinforced sections 20 and 21 to be doubly stitched. As noted previously, in a preferred embodiment, loop 22 has no reinforced section 20 or 21, with the natural engagement of tails 2 and 3 within the lumen of suture material 1, retaining tails 2 and 3.

Alternative means of inserting the cut tail 2 and the save tail 3 into the lumen of the fiber 1 to achieve a similar final assembly are also readily contemplated herein. For example, a needle or other tool can be used to guide and insert the cut tail 2 and/or save tail 3 directly into the lumen of the fiber 1 without have the tool first being inserted into the lumen. According to alternative embodiments, the cut tail 2 and save tail 3 could be inserted within the lumen and left within, without having the ends first pulled out, cut, and retracted as described above. This could be done with the step of cinching/stretching out the loop, as described above. It is preferred that the cut tail 2 and save tail 3 are inserted substantially within the lumen, and not just their ends. More specifically, it is preferred that the entire circumference of the lumen, or substantially so, is occupied with either the cut tail 2 or save tail 3, or both with respects to overlapping between the two. In a first preferred embodiment the suture loop 22 is made of USP-2 suture material and in a second preferred embodiment the suture loop is made of USP-5 material.

It is preferred that the assembly 22 is re-measured and re-stretched (e.g., at approximately 100 lbs.) if needed to achieve the final desired loop size.

Figure 15:
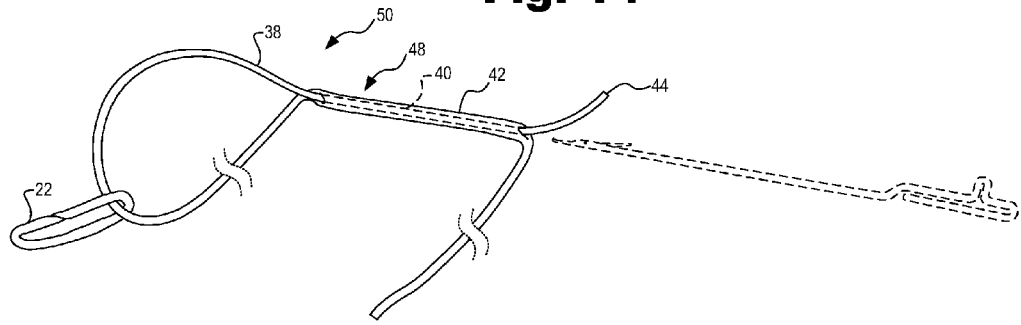
FIG. 15 is an isometric view of a partially finished suture assembly, according to the present invention.
Figure 16:
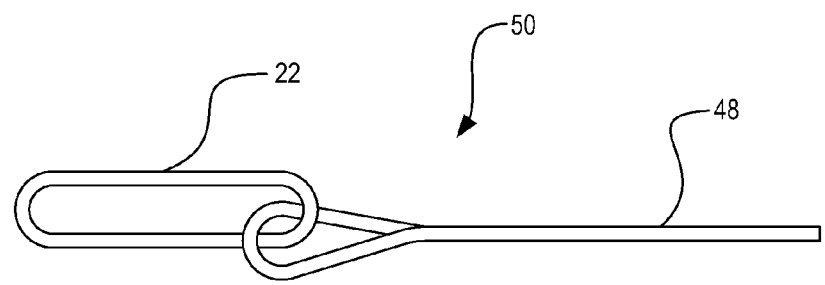
FIG. 16 is a side view of a finished suture assembly, according to the present invention.
Figure 17:
FIG. 17 is a side view of two bone screws that are used in a method of repairing a cranial cruciate ligament, according to the present invention.
Figure 18A:
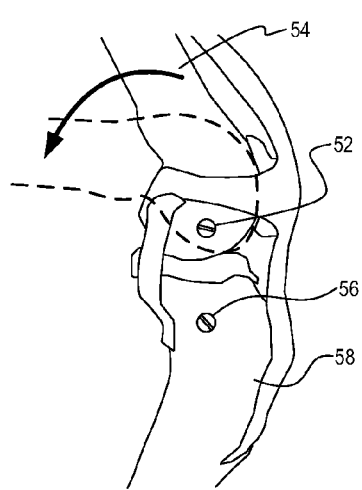
Figure 18B:
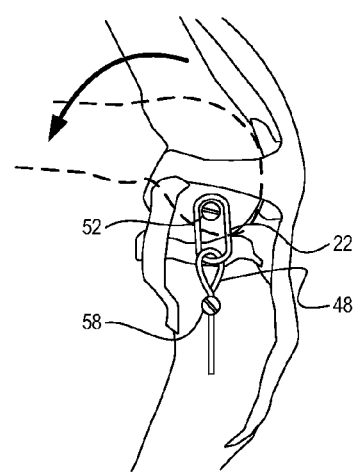

Referring to FIGS. 12-15, after loop 22 is complete, construction of assembly 50 continues with a length of suture material 30, in which an entry point 32 and an exit point 34 are defined and fluffed to facilitate entry and exit of lacing tool 7. Next (FIG. 14) suture 30 is extended through loop 22, and lacing tool 7 is introduced into length 30 at entry point 32, and out at exit point 34, and captures a free end 36 of length 30. Referring to FIG. 15, lacing tool is used to pull free end 36 through exit point 34 and entry point 32 to form a loop 38, with a first portion 40 of length 30, passing through a second portion 42 of length 30. Assembly 50 is now essentially complete, with a further step in which stitching is used to fix portion 40 inside portion 42, being performed in a preferred embodiment, and a loose end 44 being cut off. Referring to FIG. 16, at this point, assembly 50, including loop 22 and eyelet-tail element 48 is complete. In an alternative preferred embodiment, eyelet-tail element 48 is replaced by another form of tension. In one embodiment wire is folded over a portion of loop 22 and used in the same manner as element 48, in the method described below. In one embodiment this wire is made of nitinol.

Referring to FIGS. 17 and 18A-18D, a veterinary surgery to implant loop 22, so that it can absorb some of the stress normally born by the cranial (anterior) cruciate ligament is possible, using assembly 50. A first bone screw 52 is introduced into the femur 54, and a second bone screw 56, having an aperture 57 in its shank, as shown is introduced into the tibia 58. Eyelet-tail element 48 is used to pull loop 22 over the head of screw 52, so that it is interposed between the head of screw 52 and femur 54. Next, eyelet-tail element 48 is used to pull loop 22 through aperture 57, then twist loop 22, and extend a portion of it over the head of screw 56, where it is interposed between this head and the tibia. Then screw 56 may be tightened to squeeze the interposed portion of loop 22 tightly between screw head and bone. Screw 52 may be tightened, but should be left loose enough so that loop 22 can slide about it.

While a number of exemplary aspects and embodiments have been discussed above, those possessed of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A method of repairing a stifle, including a first stifle bone and a second stifle bone in engaged opposition to said first stifle bone, and comprising:
   (a) providing:
      (i) a first bone screw that includes a head and a shank having helical threads; and
      (ii) a second bone screw that includes a head and a shank having helical threads and defining an aperture therethrough, adjacent to said head;
      (iii) a suture assembly including a suture loop and an eyelet-tail suture element having an eyelet and a tail extending from said eyelet, said eyelet being engaged to said suture loop;
   (b) screwing said first bone screw into said first stifle bone;
   (c) screwing said second bone screw into said second stifle bone;
   (d) using said tail to pull said suture assembly and engage a portion of said suture loop about said shank of said first bone screw;
   (e) using said tail to pull said suture assembly and pull said suture loop through said aperture in said second bone screw; and
   (f) using said tail to pull said suture loop into engagement around said shank of said second bone screw; and
   (g) cutting away and removing said eyelet-tail suture element.

2. The method of claim 1, wherein said first stifle bone is the tibia of said stifle and said second stifle bone is the femur of said stifle.

3. The method of claim 1, wherein said first stifle bone is the femur of said stifle and said second stifle bone is the tibia of said stifle.

4. The method of claim 1, wherein said first and second bone screws are tightened after said suture loop is installed, to grip said suture loop between said screw heads and bone.

5. The method of claim 1, wherein said suture loop is twisted between being pulled through said aperture and being engaged about said shank of said second bone screw.

* * * * *